(12) United States Patent
Friesen et al.

(10) Patent No.: US 9,147,919 B2
(45) Date of Patent: Sep. 29, 2015

(54) METHODS OF PRODUCING SULFATE SALTS OF CATIONS FROM HETEROATOMIC COMPOUNDS AND DIALKYL SULFATES AND USES THEREOF

(75) Inventors: Cody A. Friesen, Fort McDowell, AZ (US); Derek Wolfe, Adrian, MI (US); Paul Bryan Johnson, Phoenix, AZ (US)

(73) Assignee: FLUIDIC, INC., Scottsdale, AZ (US)

( * ) Notice: Subject to any disclaimer, the term of this patent is extended or adjusted under 35 U.S.C. 154(b) by 0 days.

(21) Appl. No.: 13/526,058

(22) Filed: Jun. 18, 2012

(65) Prior Publication Data
US 2012/0323004 A1 Dec. 20, 2012

Related U.S. Application Data

(60) Provisional application No. 61/498,308, filed on Jun. 17, 2011.

(51) Int. Cl.
| | | |
|---|---|---|
| *C07D 265/30* | (2006.01) | |
| *C07D 295/00* | (2006.01) | |
| *H01M 12/06* | (2006.01) | |
| *C07D 471/04* | (2006.01) | |

(52) U.S. Cl.
CPC ............. *H01M 12/06* (2013.01); *C07D 471/04* (2013.01); *H01M 2300/0014* (2013.01); *H01M 2300/0045* (2013.01)

(58) Field of Classification Search
CPC ............................ C07D 265/30; C07D 295/00
USPC ................................................ 544/107, 108
See application file for complete search history.

(56) References Cited

U.S. PATENT DOCUMENTS

| | | |
|---|---|---|
| 2003/0065037 A1 | 4/2003 | Mattison et al. |
| 2005/0194561 A1 | 9/2005 | Davis |
| 2008/0251759 A1 | 10/2008 | Kalb et al. |
| 2010/0137460 A1 | 6/2010 | Bert et al. |
| 2010/0285375 A1 | 11/2010 | Friesen et al. |
| 2010/0323249 A1 | 12/2010 | Fujiwara et al. |
| 2011/0027664 A1 | 2/2011 | Burchardt |
| 2011/0027666 A1 | 2/2011 | Burchardt et al. |
| 2011/0065018 A1 | 3/2011 | Kim et al. |
| 2011/0281184 A1 | 11/2011 | Friesen et al. |
| 2011/0305959 A1 | 12/2011 | Friesen et al. |

FOREIGN PATENT DOCUMENTS

| | | |
|---|---|---|
| CN | 1946673 | 4/2007 |
| CN | 101137436 | 3/2008 |
| CN | 102 050 788 A | 5/2011 |
| EP | 1 182 196 A1 | 2/2002 |
| EP | 1 398 318 A1 | 3/2004 |
| GB | 1 297 955 A | 11/1972 |
| JP | 2005 026023 A | 1/2005 |
| WO | 20100136783 A1 | 12/2010 |

OTHER PUBLICATIONS

Wang, X., et al., "A polytetrafluoroethylene-quaternanry 1,4-diazabicyclo—[2.2.2]-octane polysulfone composite membrane for alkaline anion exchange membrane fuel cells", Intl. J. Hydrogen Energy, vol. 36 No. 16, pp. 10022-10026 (May 9, 2011).
Yan, X., et al., "Quaternized poly(ether ether ketone) hydroxide exchange membranes for fuel cells", J. Membrane Science, vol. 375, No. 1, pp. 204-211 (Mar. 22, 2011).
Stoica et al., "Anionic membrane based on polyepichlorhydrin matrix for alkaline fuel cell: Synthesis, physical and electrochemical properties", vol. 53, No. 4, pp. 1596-1603 (Oct. 30, 2007).
Park, J-S., "Development of Solid-State Alkaline Electrolytes for Solid Alkaline Fuel Cells", Macromolecular Symposia, vol. 249-250, No. 1, pp. 174-182 (Apr. 1, 2007).
Gu, S., et al., "Soluble and Highly Conductive Ionomer for High-Performance Hydroxide Exchange Membrane Fuel Cells", Angewandte Chemie Intl. Ed., vol. 48, No. 35, pp. 6499-6501 (Aug. 17, 2009).
Intl. Search Report/Written Opinion dated Dec. 3, 2012 of PCT/US2012/043000 filed Jun. 18, 2012 (15 pages).
Intl Search Report dated Nov. 28, 2012 of PCT/US2012/043013 dated Jun. 18, 2012 (15 pages).
Yao, C., et al., "Retention characteristics of organic compounds on molten salt and ionic liquid-based gas chromatography stationary phases", Journal of Chromatography, vol. 1216, No. 10, pp. 1658-1712 (Mar. 6, 2009).
Intl. Search Report/Written Opinion dated Sep. 5, 2012 of PCT/US2012/033940 filed Apr. 17, 2012 (11 pages).
Intl Search Report/Written Opinion of PCT/US2012/042955 filed Jun. 18, 2012 dated Sep. 6, 2012 (8 pages).
Final Rejection dated Oct. 17, 2013 of U.S. Appl. No. 13/448,923, filed Apr. 12, 2012 (16 pages).
Non-Final Rejection dated Oct. 19, 2013 of U.S. Appl. No. 13/448,923, filed Apr. 12, 2012 (33 pages).
Chinese Office Action dated Feb. 9, 2015 for Appln. No. 2012800247268.
Non-Final Rejection dated May 19, 2014 of U.S. Appl. No. 13/526,342, filed Jun. 18, 2012 (27 pages).
Non-Final Rejection dated Nov. 26, 2013 of U.S. Appl. No. 13/526,342, filed Jun. 18, 2012 (34 pages).
International Preliminary Report on Patentability dated Jan. 17, 2014 of PCT/US12/43000 filed Jun. 18, 2012 (9 pages).
Intl. Prel. Report on Patentability dated May 20, 2013 of PCT/US12/43013 filed Jun. 18, 2012 (18 pages).
U.S. Office Action dated Dec. 2, 2014 for U.S. Appl. No. 13/526,342.
K. Scott, Section 2—Membrane Materials, Preparation and Characterisation, In Handbook of Industrial Membranes (Second Edition), edited by K. Scott, Elsevier Science, Amsterdam, 1998, pp. 187-269, ISBN 9781856172332, http://dx.doi.org/10.1016/B978-185617233-2/50005-2. (http://www.sciencedirect.com/science/article/pii/B9781856172332500052).
U.S. Office Action dated Jul. 16, 2015 for U.S. Appl. No. 14/077,903.
Chinese Office Action dated Jun. 30, 2015 for Appln. No. 2012800400535.

*Primary Examiner* — Yong Chu
*Assistant Examiner* — Sonya Wright
(74) *Attorney, Agent, or Firm* — Pillsbury Winthrop Shaw Pittman, LLP

(57) ABSTRACT

Methods of preparing sulfate salts of heteroatomic compounds using dialkyl sulfates as a primary reactant are disclosed. Also disclosed are methods of making ionic liquids from the sulfate salts of the heteroatomic compound, and electrochemical cells comprising the ionic liquids.

19 Claims, 1 Drawing Sheet

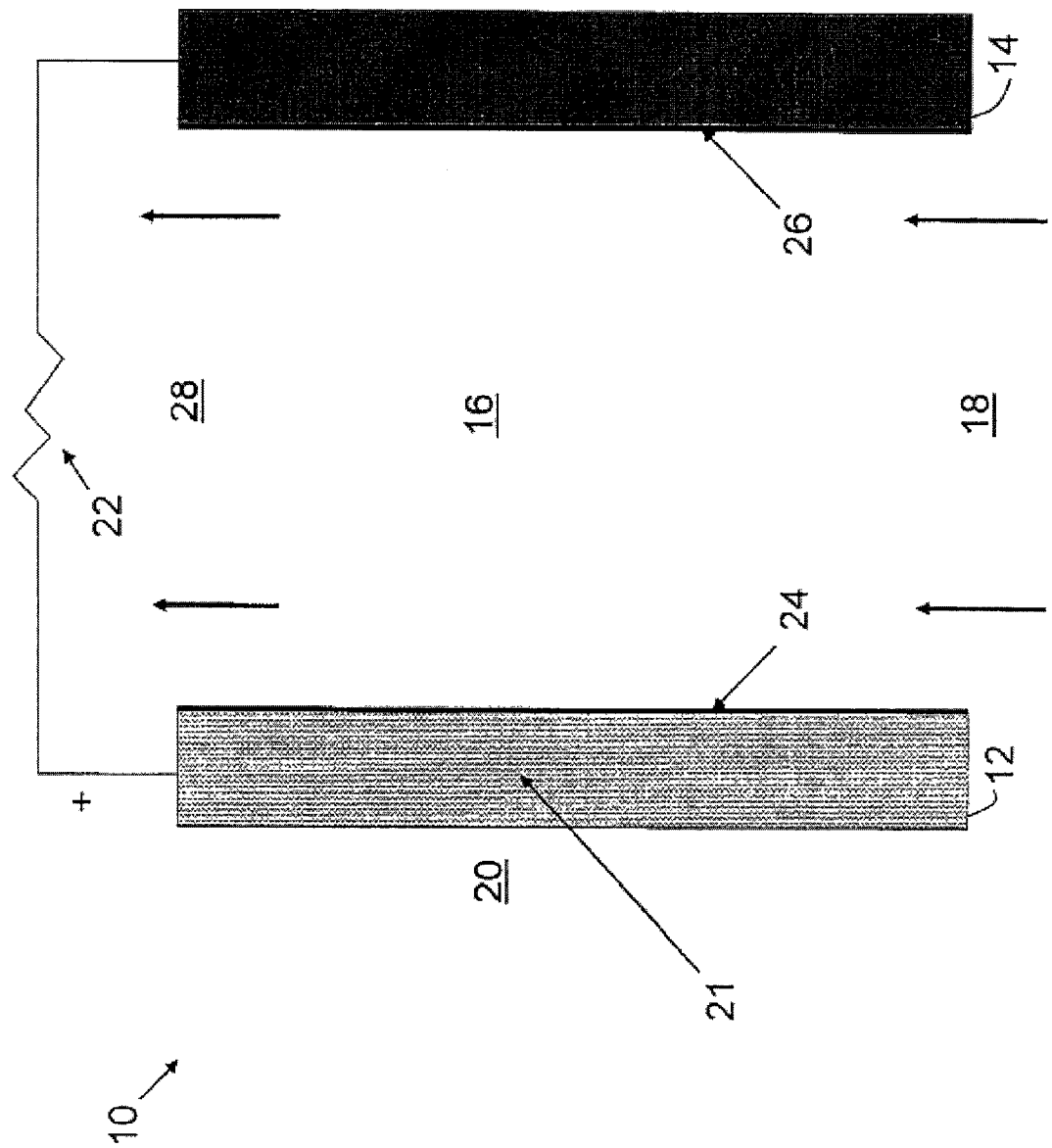

METHODS OF PRODUCING SULFATE SALTS OF CATIONS FROM HETEROATOMIC COMPOUNDS AND DIALKYL SULFATES AND USES THEREOF

REFERENCE TO PRIOR APPLICATIONS

This application claims priority to U.S. provisional application No. 61/498,308 filed 17 Jun. 2011.

GOVERNMENT FUNDING SUPPORT

This invention was made with U.S. government support under Contract No. DB-AR-0000038 awarded by the Department of Energy. The government has certain rights in the invention.

FIELD OF THE INVENTION

The embodiments relate to methods of making a sulfate salt of a heteroatomic compound using a dialkyl sulfate as a primary reactant. Embodiments also relate to methods of making ionic liquids by reacting the sulfate salt of a heteroatomic compound with a salt of a desired anion to produce an ionic liquid comprising the heteroatomic cation and desired anion.

BACKGROUND OF THE INVENTION

Ionic liquids are typically prepared from heteroatomic compounds by a two-step sequence of alkylation and anion exchange. Alkylation is generally accomplished with an alkyl chloride, bromide, or iodide. Halide salts (i.e., chloride, bromide, or iodide salts) prepared in this way are frequently ionic liquids themselves and may be appropriate for some applications. In addition, the salt of an anion other than a halide is often desirable, and there are many protocols available to accomplish anion exchange. However, there are at least two deficiencies in a typical method of ionic liquid preparation.

First, in a typical ionic liquid preparation, the heteroatomic compound must be sufficiently nucleophilic, and the alkyl halide must be sufficiently electrophilic, for alkylation to occur to a useful extent under convenient conditions.

Second, and more significantly, ionic liquids prepared by conventional methods typically are contaminated with some amount of antecedent halide inherent to the halide alkylation process, and halides are deleterious to many applications. For example, ionic liquids may be used in electrochemical devices, but halides are known to have detrimental effects on electrochemical devices, including corroding materials commonly used to construct electrochemical devices; damaging the electrochemical device through the decomposition of the halide contaminant; and reducing the cycle efficiency of the electrochemical device through undesirable side reactions with the halide contaminant.

Although halide removal to the ppm scale may often be achieved in the preparation of a hydrophobic ionic liquid, halide contamination is particularly difficult to remove in the preparation of a hydrophilic ionic liquid. For example, the residual halide concentration following one representative anion exchange from a halide salt to a representative hydrophilic ionic liquid was measured at 27 wt % (270,000 ppm). Thus, it is desirable to avoid halide alkylation when preparing ionic liquids, and particularly hydrophilic ionic liquids. As described in the present disclosure, dialkyl sulfates, which are aggressive electrophiles and readily alkylate even subdued nucleophiles (e.g., morpholines and thiazoles), can alkylate heteroatomic compounds to prepare ionic liquids that may not be readily prepared by a typical ionic liquid preparation method.

A significant detriment to the energy density of most batteries is posed by the battery's cathode. This is true for battery chemistries using, for example, lithium or nickel. Typically, oxidant is stored at the cathode at a molar charge capacity that is two to five times lower than that of the anode. Many fuel cells, on the other hand, use oxygen from the air as a source of oxidant. The existence of a continuous and virtually limitless oxidant source enables, in principle, high energy density. However, the use of hydrogen and organic fuels precludes high energy efficiencies due to problems with vapor pressure and balance-of-systems complexity, such as humidification and membrane issues. Metal-air electrochemical cells are able to combine the ultra-high anode capacity of batteries with the air-breathing cathode of fuel cells in order to achieve substantial energy densities that are relevant to modern energy demands.

Metal-air batteries typically include a fuel electrode at which metal fuel is oxidized, an air electrode at which oxygen is reduced, and an electrolyte solution for providing ion conductivity. A limiting factor with metal-air batteries is the evaporation of the electrolyte solution, particularly the evaporation of the bulk solvent, such as water in an aqueous electrolyte solution. Because the air electrode is required to be air permeable to absorb oxygen, it is also may permit the solvent vapor, such as water vapor, to escape from the cell. Over time, the cell becomes incapable of operating effectively because of this issue. Indeed, in many cell designs this evaporation issue renders the cell inoperable before the fuel is consumed. And this issue is exacerbated in secondary (i.e., rechargeable) cells, because the fuel may be re-charged repeatedly over the life of the cell, whereas the electrolyte solution is not (absent replenishment from an external source). Also, in rechargeable cells the water solvent is typically oxidized to evolve oxygen during re-charge, which may also deplete the solution.

There are other problems associated with conventional aqueous electrolyte batteries, such as water electrolysis during recharging, and self discharge. During recharge, a current is passed through the battery to reduce the oxidized fuel at the fuel electrode. Some of the current, however, electrolyzes the water resulting in hydrogen evolution (reduction) at the fuel electrode and oxygen evolution (oxidation) at the oxygen electrode as represented in the following equations:

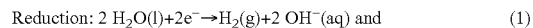

Reduction: $2\,H_2O(l)+2e^- \rightarrow H_2(g)+2\,OH^-(aq)$ and (1)

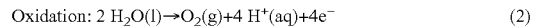

Oxidation: $2\,H_2O(l) \rightarrow O_2(g)+4\,H^+(aq)+4e^-$ (2)

In this manner, further aqueous electrolyte is lost from the battery. Additionally, the electrons that are consumed in reducing hydrogen are not available to reduce the fuel oxide. Therefore, the parasitic electrolysis of the aqueous electrolyte reduces the round trip efficiency of the secondary battery.

Self-discharge may result from impurities in the electrodes or reaction with the electrolyte. Typically, self-discharge from impurities in the electrodes is small (2-3% loss per month). The reaction of an active metal with water and/or $O_2$ dissolved in the water, however, may be quite high (20-30% per month).

To compensate for these problems, metal-air batteries with aqueous electrolyte solutions are typically designed to contain a relatively high volume of electrolyte solution. Some cell designs even incorporate means for replenishing the electrolyte from an adjacent reservoir to maintain the electrolyte level. However, either approach adds significantly to both the overall size of the cell, as well as the weight of the cell, without enhancing the cell performance (except to ensure that there is a sufficient volume of electrolyte solution to offset evaporation of the water or other solvent over time). Specifically, the cell performance is generally determined by the fuel characteristics, the electrode characteristics, the electrolyte characteristics, and the amount of electrode surface area available for reactions to take place. But the volume of electrolyte solution in the cell generally does not have a significant beneficial effect on cell performance, and thus generally only detracts from cell performance in terms of volumetric and weight based ratios (power to volume or weight, and energy to volume or weight). Also, an excessive volume of electrolyte may create a higher amount of spacing between the electrodes, which may increase ionic resistance and detract from performance.

The use of non-aqueous systems for electrochemical cells has been suggested (see, e.g., U.S. Pat. No. 5,827,602). In non-aqueous systems, the aqueous electrolyte may be replaced with an ionic liquid. Ionic liquids which contain a strong Lewis acid such as $AlCl_3$, however, are known to liberate toxic gases when exposed to moisture.

The use of low or room temperature ionic liquid rather than an aqueous electrolyte in a metal-air electrochemical cell, as described in U.S. Provisional Application Ser. No. 61/383, 510, filed Sep. 16, 2010; 61/355,081, filed Jun. 15, 2010; 61/334,047, filed May 12, 2010; 61/329,278, filed Apr. 29, 2010; 61/177,072, filed May 11, 2009, and 61/267,240, filed Dec. 7, 2009, and described in U.S. patent application Ser. No. 13/105,794, filed on May 11, 2011; Ser. No. 13/096,851, filed Apr. 28, 2011; Ser. No. 13/085,714, filed Apr. 13, 2011; and Ser. No. 12/776,962, filed May 10, 2010, the disclosures of each of which are incorporated herein by reference in their entirety. The use of a low or room temperature ionic liquid in the cell essentially eliminates the problems associated with evaporation of solvent from an electrolytic solution.

Room temperature ionic liquids have extremely low vapor pressures (some have vapor pressures that are essentially immeasurable under standard conditions) and thus experience little or no evaporation. Therefore, cells using low or room temperature ionic liquids as their ionically conductive media need not incorporate excessive volumes of solution in order to compensate for evaporation over time. Relatively small amounts of ionic liquid are sufficient to support the electrochemical reactions needed for cell operation, thereby reducing cell weight and volume and increasing power to volume/weight ratios. Also, other problems associated with solvents, such as hydrogen evolution in an aqueous solution, may be avoided. This inventive development is not conceded to be prior art and merely is described for contextual purposes to facilitate an understanding of the further development described herein.

SUMMARY OF THE INVENTION

This disclosure describes methods of producing sulfate salts of cations from heteroatomic compounds and dialkyl sulfates and uses thereof. One feature of an embodiment provides a method for preparing a sulfate salt of a heteroatomic compound comprising reacting a heteroatomic compound with an excess of diaklysulfate; hydrolyzing the product of that reaction to produce a bisulfate salt; and neutralizing the bisulfate salt to produce the sulfate salt of the heteroatomic compound.

Another feature of an embodiment provides a method for preparing an ionic liquid comprising reacting a heteroatomic compound with an excess of diaklysulfate; hydrolyzing the product of that reaction to produce a bisulfate salt; neutralizing the bisulfate salt to produce a sulfate salt of the heteroatomic compound; and reacting the sulfate salt of the heteroatomic compound with a salt of a desired anion to produce an ionic liquid comprised of the cation of the heteroatomic compound and the desired anion.

Another feature of an embodiment provides a method for preparing an ionic liquid comprising reacting a heteroatomic compound with an excess of dialkyl sulfate and hydrolyzing the product of that reaction to produce a bisulfate salt.

Another feature of an embodiment provides an electrochemical metal-air cell comprising a fuel electrode for oxidizing a metal fuel; an air electrode for absorbing and reducing gaseous oxygen; and an ionically conductive medium comprising a low temperature ionic liquid having a melting point at or below 150° C. at 1 atm, wherein the ionic liquid comprises a desired anion and a cation of the heteroatomic compound prepared in accordance with the method described above. The ionic liquid is contained in a space between the fuel electrode and the air electrode for conducting ions for supporting the electrochemical reactions at the fuel and air electrodes.

For the purposes of this application, a low temperature ionic liquid is defined as an ionic liquid having a melting point at or below 150° C. at 1 atm. These low temperature ionic liquids may also include the species known as room temperature ionic liquids, which are defined as ionic liquids having a melting point at or below 100° C. at 1 atm. Ionic liquids are also referred to as liquid salts. By definition, an ionic liquid is composed primarily of anions and cations of the salt. While an ionic liquid itself may be a solvent with respect to one or more other soluble products present in the ionic liquid, such as an additive or reactant by-product created by operation of the cell, an ionic liquid does not require the use of a solvent to dissolve the salt, as the liquid itself is "self-dissolving," i.e., it is a liquid of the electrolyte salt anions and cations by its own nature, and the use of a separate solvent to dissolve the salt is not necessary.

However, even though low temperature or room temperature ionic liquids are defined by their respective melting points at 1 atm., in some embodiments the cell may be operated in an environment with a different pressure, and thus the melting point may vary with the operating pressure. Thus, reference to a melting point at 1 atm. is used as a reference point to define these liquids, and does not imply or restrict its actual use conditions in operation.

Other objects, features, and advantages of the present invention will become apparent from the following detailed description, the accompanying drawings, and the appended claims.

BRIEF DESCRIPTION OF THE DRAWINGS

FIG. 1 is an exploded view of a cell in accordance with an embodiment of the invention;

DETAILED DESCRIPTION OF THE INVENTION

Ionic liquids generally refer to salts that form stable liquids comprising ions. That is, ionic liquids are fully dissociated, consisting essentially of negative and positive ions. Thus, ionic liquids inherently conduct electricity. Further, ionic liquids have negligible vapor pressure, low viscosity, wide liquids (up to 400° C.), high thermal stability, and a large electrochemical window (>5V). Because of these properties, ionic liquids typically will not evaporate or be consumed during the charge/discharge cycle of an electrochemical cell.

Ionic liquids generally exist in two forms: protic and aprotic. Protic ionic liquids have available protons which may be oxidized or reduced or may coordinate with negative ions, such as reduced oxygens. Some examples of protic ILs are synthesized from combinations of anions tetrachloroaluminate, bis(trifluoromethylsulfonyl)imide, methylsulfonate, nitrate, and acetate, and cations triethylammonium, diethylmethylammonium, dimethylethylammonium, dimethylethylammonium triflate, ethylammonium, α-picolinium, pyridinium, and 1,8-bis(dimethylamino)naphthalene, 2,6-di-tert-butylpyridine, and derivatives of the guanidines. Aprotic ionic liquids, however, generally do not have proton activity. Some example of aprotic room temperature ionic liquids are synthesized from combinations of anions selected from chloride (Cl$^-$), hexafluorophosphate (PF$_6^-$), iodide, tetrfluoroborate, bis(trifluoromethylsulfonyl)imide (C$_2$F$_6$NO$_4$S$_2^-$) (TFSI), trifluoromethanesulfonate (CF$_3$O$_3$S$^-$), and cations selected from imidazolium, sulfonium, pyrrolidinium, quaternized ammonium or phosponium and their derivatives. Despite a lack of proton activity, an aprotic ionic liquid can comprise a proton. For example, an aprotic ionic liquid can comprise at least one cation that has at least one strongly bound proton thereto. Many other options of ionic liquids exist, and these lists of examples are not intended to be limiting in any way.

One preferred embodiment of the present invention includes a method of preparing a sulfate salt of a heteroatomic compound. The expression "heteroatomic compound" is generally known in the art, and is used herein to denote its conventional meaning, including compounds containing a heteroatom, such as a non-carbon atom. In one embodiment, a heteroatomic compound is an aliphatic, alicyclic, or aromatic compound that includes a non-carbon atom, such as oxygen, nitrogen, phosphorus, or sulfur. A preferred reaction for producing a sulfate salt of a heteroatomic compound, which is embodied in the present invention, can be represented by the following general equation:

(1)

wherein $XR^1 \ldots R^y$ is an aliphatic, acyclic, or aromatic heteroatomic compound that can be linear or can form a hetero or heteroatomic ring; X=any atom other than C or H, and preferably N, P, or S; and $R^1 \ldots R^y$ are functional groups that can be either an inorganic or organic functional group, including H. The identity of X determines how many functional groups $R^1 \ldots R^y$ are associated with the heteroatomic compound. Functional groups $R^1 \ldots R^y$ need not be identical. $R''$ and $R^z$=alkyl, including but not limited to substituted and unsubstituted C$_1$-C$_{20}$ alkyl, or substituted and unsubstituted aralkyl, more preferably a methyl or methyl group. $R''$ and $R^z$ may be the same or different and represent any alkyl group.

In a particularly preferred embodiment, the reaction route for producing a sulfate salt of a heteroatomic compound comprises: reacting a heteroatomic compound with an excess of dialkyl sulfate to produce an alkylsulfate salt of the heteroatomic compound, hydrolyzing the alkylsulfate salt to produce a bisulfate salt of the heteroatomic compound, and neutralizing the bisulfate salt to produce a sulfate salt of the heteroatomic compound, which then can be used to prepare the ionic liquid by reaction with a salt of a desired anion.

The overall reaction is shown below:

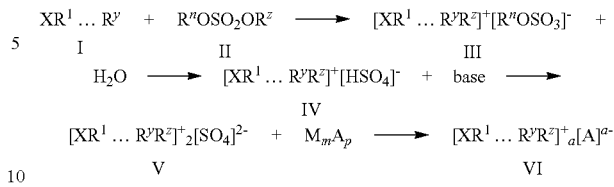

The various substituents will be described in more detail below with respect to each portion of the process.

The advantages of this process include being halide-free; making use of dialkyl sulfates, which are powerful alkylating agents that can quaternize heteroatomic compounds that are otherwise difficult to quaternize; and producing consistent batches of the resulting ionic liquid. Other advantages, features, and objects of the present invention will become apparent from the description of the reaction steps, examples, and the appended claims.

In preferred embodiments, the heteroatomic compound is selected from the group consisting pyrrolidines, morpholines, piperidines, piperazines, quinuclidines, bicyclic amines, amidines, guanidines, alkanolamines, monoalkylamines, dialkylamines, trialkylamines, pyrroles, imidazoles, pyrazoles, triazoles, thiazoles, oxazoles, pyridines, imidazopyridines, imidazopyrimidines, monoalkylphosphines, dialkylphosphines, trialkylphosphines, monoalkylphosphites, dialkylphosphites, trialkylphosphites, phosphorus monoamines, phosphorus diamines, phosphorus triamines, mercaptans, thiophenes, dihydrothiophenes, tetrahydrothiophenes, thioethers, dialkylsulfoxides, and combinations thereof. In another preferred embodiment, $R''OSO_2R^z$ is a dialkyl sulfate, in which $R''$ and $R^z$ may be the same or different and represent any alkyl group. Preferably, the dialkyl sulfate is dimethyl sulfate or diethyl sulfate.

The initial reaction preferably includes reacting a heteroatomic compound with an excess of diakylsulfate to produce an alkylsulfate salt of the heteroatomic compound. The reaction is shown in the following equation:

$$XR^1 \ldots R^y + R''OSO_2OR^z \rightarrow [XR^1 \ldots R^yR^z]^+ [R''OSO_3]^-$$ (2)

wherein $XR^1 \ldots R^y$ is the heteroatomic compound; the substituents $R^1$-$R^y$ may include one or more organic and/or inorganic functional groups, hydrogen, may be the same or different, and together with X denote the heteroatomic compound; $R^z$ and $R''$=alkyl, may be the same or different, and include, but are not limited to substituted and unsubstituted C$_1$-C$_{20}$ alkyl, substituted and unsubstituted aralkyl, more preferably a methyl or ethyl group; X=any atom other than C or H, including but not limited to N, P, or S, or SO, and can be aliphatic, alicyclic, or aromatic. $[XR^1 \ldots R^yR^z]^+[R''OSO_3]^-$ is the resulting alkylsulfate salt of the heteroatomic cation. The positive charge on $[XR^1 \ldots R^yR^z]^+$ resides on X.

A second reaction may include hydrolyzing the alkylsulfate salt to produce a bisulfate salt of the heteroatomic compound, as shown in the following equation:

(3)

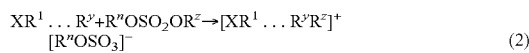

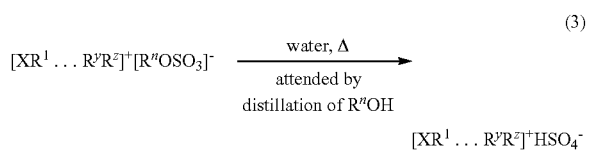

wherein $[XR^1 \ldots R^yR^z]^+$ is the heteroatomic cation; the substituents $R^1$-$R^y$ may include one or more organic and/or inorganic functional groups, hydrogen, may be the same or different, and together with X denote the heteroatomic compound; $R^z$ and $R''$=alkyl, may be the same or different, and include, but are not limited to substituted and unsubstituted $C_1$-$C_{20}$ alkyl, substituted and unsubstituted aralkyl, more preferably a methyl or ethyl group; X=any atom other than C or H, including but not limited to N, P, or S, or SO, and can be aliphatic, alicyclic, or aromatic. $[XR^1 \ldots R^yR^z]^+[R''OSO_3]^-$ is the resulting alkylsulfate salt of the heteroatomic cation. The positive charge on $[XR^1 \ldots R^yR^z]^+$ resides on X. The positive charge on $[XR^1 \ldots R^yR^z]^+$ resides on X. The reaction, which is carried out in the presence of water, is preferably heated to close to the boiling point of water.

The hydrolysis of the alkylsulfate salt to form the bisulfate salt of the heteroatomic compound shown above in equation 3 proceeds to completion, which is an unexpected result. Typically, hydrolysis of an alkylsulfate is an unproductively slow reaction. For example, the hydrolysis of methylsulfate has $k_{25°C}$=2.2×10$^{-11}$ M$^{-1}$ s$^{-1}$ at pH=7. (See Wolfenden and Yuan, *PNAS* 2007 83-86.) Although hydrolysis of methylsulfate proceeds more than 1000 times faster in acidic conditions, and four times faster in alkaline conditions than in acidic conditions (see Wolfenden and Yuan), the hydrolysis of the alkylsulfate salt illustrated above in Equation 3 above was not expected to proceed to completion in acid in a reasonable amount of time. Not intending to be bound by any theory of operation, it is believed that when the excess dialkyl sulfate reacts with water, the excess dialkyl sulfate is converted first to alkylsulfuric acid, then to a mixture of alkylsulfuric acid and sulfuric acid, and finally to sulfuric acid. This belief is supported by the observation that the reaction mixture becomes increasingly acidic, to a pH of below about −2. It is believed that these acids catalyze the hydrolysis of the alkylsulfate salt. It is further believed, again without intending to be bound by any theory of operation, that removing the alcohol by-product of the hydrolysis ($R''OH$ according to equation 3 above) further drives the hydrolysis to completion.

A third reaction may involve neutralizing the bisulfate salt produced in the second reaction to produce a sulfate salt of the heteroatomic compound, as shown in the following equation:

(4)

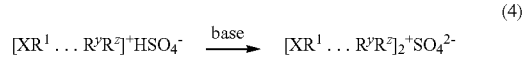

wherein $[XR^1 \ldots R^yR^z]^+$ is the heteroatomic cation; the substituents $R^1$-$R^y$ may include one or more organic and/or inorganic functional groups, hydrogen, may be the same or different, and together with X denote the heteroatomic compound; $R^z$ and $R''$=alkyl, may be the same or different, and include, but are not limited to substituted and unsubstituted $C_1$-$C_{20}$ alkyl, substituted and unsubstituted aralkyl, more preferably a methyl or ethyl group; X=any atom other than C or H, including but not limited to N, P, or S, or SO, and can be aliphatic, alicyclic, or aromatic. The positive charge on $[XR^1 \ldots R^yR^z]^+$ resides on X. The base preferably is sodium bicarbonate.

The by-product of the reaction described in equation 4 above, is a sulfate salt (preferably sodium sulfate) that precipitates out of solution upon the addition of an antisolvent. The sulfate salt of the heteroatomic compound then may be isolated and purified by standard bench techniques, including but not limited to filtration and crystallization. The sulfate salt of the heteroatomic compound, upon isolation, preferably is substantially pure.

In another preferred embodiment of the invention, the sulfate salt of a heteroatomic compound may be reacted with a salt of a desired anion to produce ionic liquids with the cation of the heteroatomic compound and the desired anion. This embodiment is shown in the following equation:

(5)

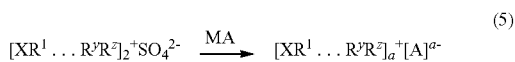

wherein $[XR^1 \ldots R^yR^z]^+$ is the heteroatomic cation; the substituents $R^1$-$R^y$ may include one or more organic and/or inorganic functional groups, hydrogen, may be the same or different, and together with X denote the heteroatomic compound; $R^z$ and $R''$=alkyl, may be the same or different, and include, but are not limited to substituted and unsubstituted $C_1$-$C_{20}$ alkyl, substituted and unsubstituted aralkyl, more preferably a methyl or ethyl group; X=any atom other than C or H, including but not limited to N, P, or S, or SO, and can be aliphatic, alicyclic, or aromatic; and MA is a salt of a desired anion, wherein M is preferably an alkali metal, an alkaline earth metal, or ammonium ($NH_4^+$), and most preferably sodium, and A is an anion. It is preferred that A is an anion selected from the group consisting of phosphate, halophosphates, especially hexafluorophosphate, alkylphosphates, arylphosphates, nitrate, sulfate, bisulfate, alkylsulfates, arylsulfates, perfluorinated alkyl- and arylsulfates, sulfonate, alkylsulfonates, arylsulfonates, perfluorinated alkyl- and arylsulfonates, especially trifluoromethylsulfonate, tosylate, perchlorate, tetrachloroaluminate, heptachlorodialuminate, tetrafluoroborate, alkylborates, arylborates, amides, especially perfluorinated amides, dicyanamide, saccharinate, thiocyanate, carboxylates, acetates, preferably trifluoroacetate, and bis(perfluoroalkylsulfonyl)amide anions. Exemplary anions include, but are not limited to, chloride (Cl$^-$), hydroxide (OH$^-$) hexafluorophosphate (PF$_6$O), iodide, other halides, tetrafluoroborate, bis(trifluoromethylsulfonyl)imide ($C_2F_6NO_4S_2^-$), trifluoromethanesulfonate ($CF_3O_3S^-$ $CF_3SO_3^-$; TfO$^-$), dicyanamide (N(CN)$_2^-$; dea), benzoate, acesulfame, saccharinate, and methanesulfonate. The positive charge on $[XR^1 \ldots R^yR^z]^+$ resides on X. Other anions include those described in, for example, co-pending U.S. patent application Ser. No. 13/448,923, entitled: "Ionic Liquids Containing Sulfonate Ions," filed on Apr. 17, 2012, the disclosure of which is incorporated by reference herein in its entirety. Suitable anions include, for example, isethionate ([ise]), taurinate ([tau]), 3-morpholinopropanesulfonate (MOPS), 4-(2-hydroxyethyl)-1-piperazinepropanesulfonate (HEPPS, EPPS), 1,4-piperazinediethanesulfonate (PIPES), N-(2-acetamido)-2-aminoethanesulfonate (ACES), N-cyclohexyl-3-aminopropanesulfonate (CAPS), 4-(2-hydroxyethyl)-1-piperazineethanesulfonate (HEPES), 2-[(2-hydroxy-1,1-bis(hydroxymethyl)ethyl)amino]ethanesulfonate (TES), N-[tris(hydroxymethyl)methyl]-3-aminopropanesulfonate (TAPS), 3-(N-tris[hydroxymethyl]methylamino)-2-hydroxypropanesulfonate (TAPSO), and mixtures thereof.

The reaction shown in equation 5 preferably is carried out in a solvent such as an alcohol, preferably ethanol or "reagent alcohol," which is approximately 90% ethanol, 5% isopropanol, and 5% methanol, and is sold by Fisher Scientific. Other viable solvents include methanol and tetrahydrofuran.

In accordance with another embodiment, there is provided a metal-air low temperature ionic liquid cell. Reference may be made to U.S. Patent Application Ser. Nos. 61/267,240 and 12/776,962 for further details concerning the construction and operation of a metal-air low temperature ionic liquid cell, the entirety of which is incorporated herein.

In a metal-air battery, the metal is the fuel. That is, during discharge the metal is oxidized at the anode, providing electrons which can be used for electrical work. The oxidation reaction may be represented by the following equation:

$$Metal \rightarrow Metal^{n+} + (n)e^-$$

The metal fuel may be of any type, and may be electrodeposited, absorbed, physically deposited, or otherwise provided on or constituting the fuel electrode. The fuel may be of any metal, including alloys or hydrides thereof, for example. For example, the fuel may comprise transition metals, alkali metals, alkali earth metals, and other or "poor" metals. Transition metals include, but are not limited to zinc, iron, manganese, and vanadium. The most common alkali metal is lithium but other alkali metals may be used. The other metals include, but are not limited to magnesium, aluminum and gallium. As used herein, the term metal fuel refers broadly to any fuel comprising a metal, including elemental metal, metal bonded in a molecule or complex, including oxides, metal alloys, metal hydrides, etc. The fuel electrode may be formed of the metal fuel as the electrode body itself in some embodiments.

The fuel electrode may have any construction or configuration. For example, the fuel electrode may be a porous structure with a three-dimensional network of pores, a mesh screen, a plurality of mesh screens isolated from one another, or any other suitable electrode. The fuel electrode includes a current collector, which may be a separate element, or the body on which the fuel is received may be electroconductive and thus also be the current collector. In an embodiment, the fuel electrode is laminated, bonded, or attached to a backing that provides the external surface of the fuel electrode. This backing may be liquid impermeable or essentially impermeable to the ionic liquid to prevent the ionic liquid from permeating outwardly through the fuel electrode via its external surface. More preferably, the backing is also impermeable to air, and particularly oxygen or other oxidant, to prevent any undesirable parasitic reaction, such as oxidant reduction in the presence of the fuel oxidation that occurs at the electrode during discharge.

Further details regarding metal fuels and fuel electrodes may be found in U.S. patent application Ser. Nos. 12/385,217, 12/385,489, 12/885,268, 12/901,410, 12/631,484, 12/549,617, 13/019,923, 13/028,496, 61/193,540, 61/301,377, 61/323,384, 61/329,278, 61/365,645, 61/394,954, 61/358,339, 61/383,510 and 61/243,970, the disclosures of each of which is incorporated by reference herein in their entirety.

During discharge, oxygen at the air electrode is reduced, consuming electrons. There are several possible mechanisms for oxygen reduction. The oxygen reduction reaction may occur, for example, via one of the three mechanisms discussed below. Other mechanisms, however, may occur depending on the chemical system (ionic liquid, electrode materials) chosen.

A first possible and non-limiting mechanism is a four-electron oxygen reduction reaction (ORR) where the product is a fully reduced oxygen dianion. The four-electron oxygen reduction reaction may be represented by the following equation:

$$O_2 + 2H_2O + 4e^- \rightarrow 4OH^-$$

Depending on the specific chemistry of the system, this reaction may form a soluble product or result locally in the formation of an insoluble metal-oxide.

In this reaction, the anions liberated may serve to mediate continued anode reaction. Relative to the other oxygen reduction mechanisms, the four-electron oxygen reduction reaction has the advantages of increased energy density and extracting the maximum number of electrons per oxygen molecule.

A second possible and non-limiting mechanism is a two-electron peroxide route. An examples of this mechanism may be represented by the following equation:

$$Zn^{2+} + O_2 + 2e^- \rightarrow ZnO_2$$

This mechanism has the advantage of relatively low overpotentials for the peroxide reaction. It also tends to have enhanced rechargeability relative to the first mechanism. The two-electron peroxide mechanism, however, results in lower energy density at the oxygen electrode battery relative to a four-electron process.

A third possible and non-limiting mechanism is a mixed two-electron/four-electron ORR that capitalizes on the reducing power of certain aliovalent cations. An examples of this mechanism may be represented by the following equation:

$$Mn^{2+} + O_2 + 2e^- \rightarrow MnO_2$$

The nuance in this mechanism is that the product involves fully reduced $O^{2-}$ species generated by the reducing power of the aliovalent metal. In this example, $Mn^{2+}$ ends up in the $Mn^{4+}$ state on the right. This mechanism has the advantage of lower overpotentials due to reducing power of the aliovalent cation. Further, aliovalent metals may be used to make more efficient cells. The mixed two-electron/four-electron mechanism, however, results in a lower energy density battery relative to a four-electron process.

Air electrodes are typically porous structures made of polytetrafluoroethylene (PTFE) materials such as Teflon®. Preferably, the air electrode material has a high degree of solvophobicity with the electrolyte. Solvophobicity within the air electrode serves the dual roles of "wet-proofing" (i.e. preventing liquid electrolyte from leaving the cell) and improving access of the oxygen in the air to the oxygen reduction reaction catalyst within the porous structure. Access to the catalyst is enhanced by solvophobicity due to an increase in the triple-junction line length of air-catalyst-electrolyte. The increase in the triple junction line length reduces transport limitations. While a strong solvophobic character is advantageous, however, including solvophilic constituents in the electrode improves the tortuosity of the triple junction, improving superficial reaction site density.

FIG. 1 illustrates a low temperature ionic liquid (IL) electrochemical cell ("electrochemical cell"), generally indicated at 10, according to the embodiments of the present invention. As illustrated and described below, the electrochemical cell 10 includes a plurality of electrodes including a first electrode 12 and a second electrode 14. In other embodiments, the first electrode or the second electrode of the electrochemical cell 10 may be provided by configurations other than a single electrode. In the non-limiting embodiment illustrated in FIG. 1, the first electrode 12 is a cathode, and more specifically an air cathode, and will be referred to hereinafter as an air electrode 12. The second electrode 14 is an anode, and will be referred to hereinafter as a metal electrode 14. In an embodiment, and as described below, the electrochemical cell 10 may generate electricity by virtue of an oxidation half-reaction of a fuel at the metal electrode 14 in parallel, that is, substantially at the same time, with a reduction half-reaction of an oxidizer 20 at the air electrode 12. The illustrated embodiment is not intended to be limiting in any way.

The air electrode 12 and the metal electrode 14 preferably are spaced apart to form a gap 16 therebetween. A room temperature ionic liquid (RTIL), generally indicated at 18, may flow along the gap 16 so that the RTIL 18 may contact both the air electrode 12 and the metal electrode 14 at the same time. In an embodiment, it should be understood that the electrochemical cell 10 may be oriented in any way, and the RTIL may flow in directions other than what is illustrated. Thus, any directional references are made with regard to the orientation as shown in FIG. 1, and are not intended to limit a working embodiment to any particular orientation. In other embodiments, the RTIL 18 may be static with no flow at all. The RTIL 18 may make contact with the air electrode 12 at an air electrode/RTIL interface 24. The RTIL 18 may make contact with the metal electrode 14 at a metal electrode/RTIL interface 26. In alternative embodiments, the RTIL does not flow. That is, no mechanism for forced flow is included in the cell.

As alluded to above, a reduction half-reaction may take place at the air electrode 12. In an embodiment, an oxidizer 20 may be reduced through the reduction half-reaction at the air electrode 12. For non-limiting illustration purposes, the electrons from the metal electrode 14 may flow to an external circuit 22 (i.e., a load) and return to the air electrode 12 to facilitate the reduction of the oxidizer 20. The oxidizer 20 is reduced on the air electrode 12 at oxidizer reduction reaction sites 21. In an embodiment, a catalyst is used to facilitate the oxidizer reduction half-reaction at the oxidizer reduction reaction sites 21. The air electrode 12 may include catalyst material, such as manganese oxide, nickel, pyrolized cobalt, activated carbon, silver, platinum, or any other catalyst material or mixture of materials with high oxygen reduction activity for catalyzing reduction of the oxidizer, which will be discussed below. In an embodiment, the air electrode 12 may be porous and the porous body with a high surface area may comprise the catalyst material.

In an embodiment, the air electrode 12 may be a passive or "breathing" air electrode 12 that is passively exposed, such as through windows or openings to an oxidizer source (typically oxygen present in ambient air) and absorbs the oxidizer 20 for consumption in the electrochemical cell 10 reactions. That is, the oxidizer 20, will permeate from the oxidizer source into the air electrode 12. Thus, the oxidizer 20 need not be actively pumped or otherwise directed to the air electrode 12, such as via an inlet. Any part of the air electrode 12 by which the oxidizer 20 is absorbed or otherwise permeates or contacts the air electrode 12 may be generically referred to as an "input." The term input may broadly encompass all ways of delivering oxidizer to the air electrode 12 for the oxidizer reduction half-reaction at the oxidizer reduction reaction sites 21 on the air electrode 12.

By means of a non-limiting illustration, the air electrode 12 may be a gas permeable electrode having an outer surface exposed to ambient air such that the oxidizer 20 comprises oxygen that permeates the air electrode 12. Similarly, the air electrode 12 may comprise a barrier membrane on the outer surface of the air electrode 12 that is gas permeable and liquid impermeable so as to permit permeation of the oxidizer 20 via the outer surface of the air electrode 12 and prevent the RTIL 18 from flowing through the outer surface of the air electrode 12. In an embodiment, the air electrode 12 may be a porous body covered on the inner side by a liquid permeable layer through which the RTIL 18 may pass through so that the low temperature IL 18 may contact the porous body.

The relationship between the RTIL 18 and the air electrode 12 may impact the overall energy density of the electrochemical cell 10. For that reason, the vapor pressure and surface tension characteristics of the RTIL 18 in view of the air electrode 12 should be carefully selected. For instance, in an embodiment, the air electrode 12 may repel the RTIL 18 so that it may prevent the RTIL 18 from wicking, that is, flowing in a capillary-like manner through the air electrode 12. In another embodiment, the air electrode 12 may be designed with porosity to absorb the RTIL so that it exposes the RTIL to more air electrode 12 surface area for purposes of enabling the desired electrochemical reactions at the air electrode 12. The air electrode 12 may support catalyst decoration at the oxidizer reduction reaction sites 21 to improve the efficiency of the reaction. In an embodiment, the catalyst may be decorated with metal ions which may enhance the activity of the catalyst in catalyzing the oxidizer reduction reaction at the oxidizer reduction reaction sites 21 on the air electrode 12. The air electrode 12 may have a high ionic conductivity to provide reactants and remove products of the oxidizer reduction reaction from the air electrode 12. In an embodiment, the air electrode 12 may have high electrical conductivity character to carry electrons from the external load 22 to the oxidizer reduction reaction sites 21. The air electrode 12 and RTIL 18 characteristics may be further defined.

In an embodiment, the metal-oxide by-products 28 may be formed at the metal electrode 14. Whereas reduced oxidizer ions in an aqueous electrolyte coordinate, that is, donate electrons to water molecules to form water, peroxides and/or hydroxides, and thereby increase problems with vapor pressure and corrosion, in this non-limiting embodiment, the RTIL 18 may promote both the oxidizer reduction reaction at the air electrode 12 and the conduction of the reduced oxidizer ions to the metal electrode 14. In support of this result, the RTIL 18 may contain soluble species that interact with the reduced oxidizer ions, with the RTIL 18 typically being protic. The RTIL 18 may also support the reduced oxidizer ions as they migrate to the metal electrode 14. By means of a non-limiting illustration, the migration of the reduced oxidizer ions may refer to transport of the reduced oxidizer ions via convection transport, or conduction transport or diffusion transport. The RTIL 18 may also support the oxidized metal-fuel ions remaining at the metal electrode 14. In doing so, the RTIL 18 promotes the reaction between the reduced oxidizer ions and the oxidized metal-fuel ions to produce the metal-oxide by-products 28. In an embodiment, the metal-oxide by-products 28 may be stored at the metal electrode 14. In an embodiment where the metal-oxide by-product 28 is stored at the metal electrode 14, this embodiment is best used as a primary (i.e., non-rechargeable) battery, as the oxygen is stored at the metal electrode 14 and is not locally available to an oxygen evolving electrode for oxidation of the reduced oxygen species.

The storage of the metal oxide locally at the air electrode is facilitated by the air electrode 12 having a pore size in at least the regions contacting the ionic liquid sufficient to contain the oxide within the air electrode 12 body. That is, the pore size may be dependent on the size of the oxide. A network of such pores may increase the storage capacity of the air electrode 12.

In an embodiment, the oxidizer source is ambient air, and the oxidizer 20 is oxygen. In an embodiment, oxygen as the oxidizer 20 may be reduced at the air electrode 12 to form reduced oxygen ions. In an embodiment, the oxygen may be supplied from an evolved oxygen recovery system used in a regenerative electrochemical cell. Other examples of electrochemical cells that may be useful embodiments of the invention herein are shown, for example, in U.S. patent application Ser. No. 12/549,617, filed on Aug. 28, 2009, which is incorporated herein by reference in its entirety.

The electrolytes of the present invention may be used in other cell configurations. An alternate cell configuration, for example, comprises a compact wound cell illustrated in U.S. Patent Application Nos. 61/267,240 and 12/776,962, hereby incorporated by reference in their entirety.

Because of evaporation, water electrolysis during recharging, and self-discharge, aqueous electrolytes are problematic for metal air batteries. These problems not only result in a loss of electrolyte but also a reduction in the round trip efficiency of a rechargeable battery. The use of an ionic liquid electrolyte reduces or may eliminate some of these problems. Even with an ionic liquid electrolyte, however, the presence of water may cause the release of toxic gases and/or cause self-discharge. On the other hand, an ionic liquid electrolyte according to embodiments of the invention may include small amounts of water. For example, water contents of 10-100 ppm have been found to improve oxygen reduction of aprotic systems without causing unacceptable self-discharge or release of toxic gases.

The forgoing embodiments have been provided solely to illustrate example of the present invention and should not be considered limiting. To the contrary, the present invention encompasses all modifications, substitutions, alterations, and equivalents with in the spirit and scope of the appended claims.

EXAMPLES

The embodiments of the present invention illustrated below are provided solely to illustrate the reaction principles of the present invention and should not be regarded as limiting. To the contrary, the present invention is intended to encompass all modifications, alterations, substitutions, and equivalents within the spirit and scope of the appended claims.

Example 1

1-Propanaminium,2-(hydroxymethyl)-N,N,N,2-tetramethyl sulfate

The sulfate salt of 1-propanaminium,2-(hydroxymethyl)-N,N,N,2-tetramethyl- may be synthesized as shown in the reaction sequences below. About 22.595 g (25 ml) of amino alcohol, available from TCI America, Portland, Oreg. was alkylated with about 33 ml of dimethyl sulfate, available from Sigma-Aldrich, St. Louis, Mo. to produce the methyl sulfate salt Alkylation:

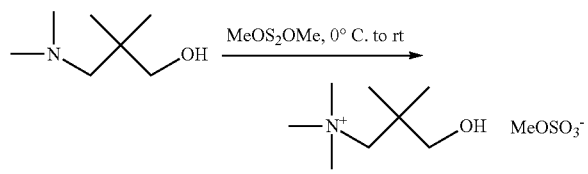

Hydrolysis: The methyl sulfate salt from the alkylation reaction above then was hydrolyzed to produce the bisulfate salt in accordance with the following reaction:

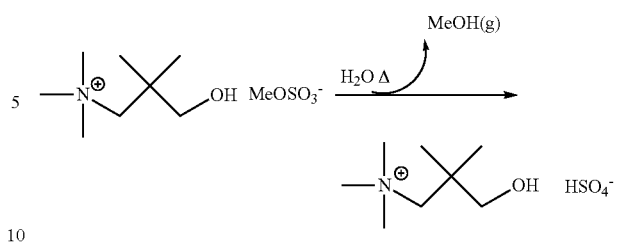

Neutralization and purification: The bisulfate salt from the hydrolysis reaction then was neutralized in a 9 wt % sodium carbonate (430.304 g), and the resulting sodium sulfate was precipitated by the addition of ethanol.

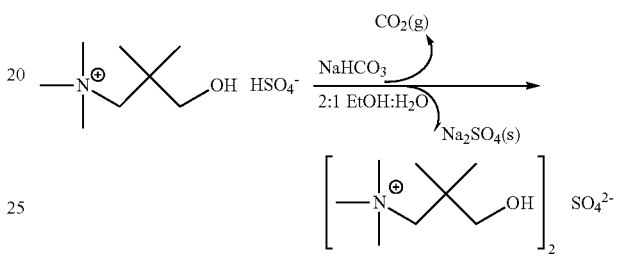

The above reactions produced about 33.030 grams of 1-propanaminium,2-(hydroxymethyl)-N,N,N,2-tetramethyl-sulfate salt. This salt then can be converted to an ionic liquid by reacting the sulfate salt produced above with a salt of a desired ion to produce an ionic liquid comprising the cation of the heteroatomic compound and the desired anion.

Example 2

N-Ethyl-N-methylmorpholinium sulfate

The sulfate salt of N-ethyl-N-methylmorpholinium is synthesized as below:

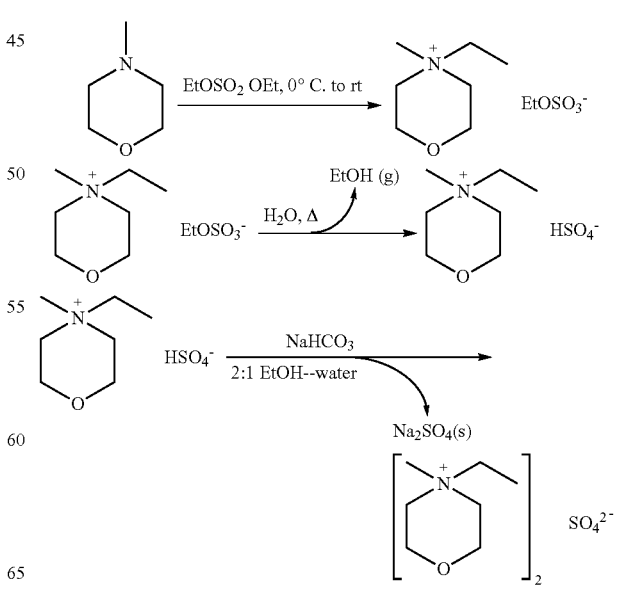

Example 3
1-Ethyl-2,3-dimethylimidazolium sulfate
The sulfate salt of 1-ethyl-2,3-dimethylimidazolium may be synthesized as below:
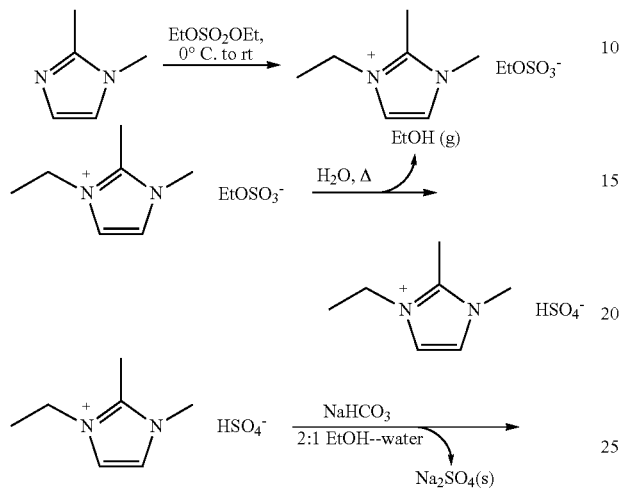
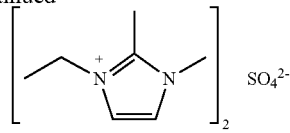
Examples 4-35
Various heteroatomic sulfate salts can be prepared in accordance with the following reaction:
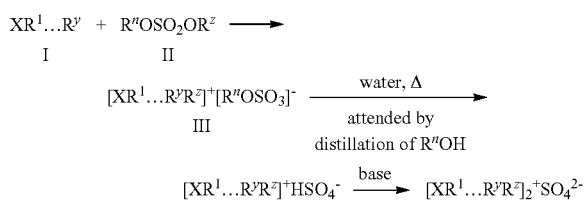
The respective substituents and compounds I-V are shown in the tables below:

ALIPHATIC EXAMPLES

| Ex. No. | I | | | | | | II | | | III |
|---|---|---|---|---|---|---|---|---|---|---|
| | X | $R^1$ | $R^2$ | $R^3$ | name | CAS no | CAS no | z | n | |
| 4 | N | Et | Et | Et | triethylamine $NC_{222}$ | | | Me | Me | triethylmethylammonium methylsulfate  [$NC_{2221}$][$MeOSO_3$] |
| 5 | N | Bu | Bu | Bu | tributylamine $NC_{444}$ | | | Et | Et | tributylethylammonium ethylsulfate  [$NC_{4442}$][$EtOSO_3$] |
| 6 | P | Bu | Bu | Bu | tributylphosphine $PC_{444}$ | | | Et | Et | tributylethylphosphonium ethylsulfate  [$PC_{4442}$][$EtOSO_3$] |
| 7 | P | n-$C_4H_{13}$ | n-$C_4H_{13}$ | n-$C_4H_{13}$ | trihexylphosphone $PC_{666}$ | | | Me | Me | trihexylmethylphosphonium methylsulfate  [$PC_{6662}$][$MeOSO_3$] |
| 8 | P | $NMe_2$ | $NMe_2$ | $NMe_2$ | hexamethylphosphorus triamide | | | Me | Me | tris(dimethylamino)methylphosphonium methylsulfate |

$$R^1 \underset{R^2}{\overset{R^3}{\diagdown}} X \diagup$$

-continued

| # | X | R¹ | R² | name | | structure name |
|---|---|---|---|---|---|---|
| 9 | P | NMe₂ | NMe₂ | hexamethylphosphorus triamide hmpt | Et Et | tris(dimethylamino)ethylphosphonium ethylsulfate [C₂hmpt][EtOSO₃] |
| 10 | P | OMe | OMe | trimethylphosphite P(OMe)₂ | Et Et | ethyltrimethoxyphosphonium ethylsulfate [P(Et)(OME)₃][EtOSO₃] |
| 11 | S | Me | n/a | dimethylsulfide dms | Et Et | [C₂dms][EtOSO₃] |
| 12 | SO | Me | n/a | dimethylsulfoxide dmso | Me Me | trimethylsulfoxonium methylsulfate [C₁dmso][MeOSO₃] |

Row 9 above also includes: hmpt — [C₁hmpt][MeOSO₃]

-continued

| Ex. No. | IV | V |
|---|---|---|
| 4 | triethylmethylammonium bisulfate [NC₂₂₂₁][HSO₄] | triethylmethylammonium sulfate [NC₂₂₂₁]₂[SO₄] |
| 5 | tributylethylammonium bisulfate [NC₄₄₄₂][HSO₄] | tributylethylammonium sulfate [NC₄₄₄₂]₂[SO₄] |
| 6 | tributylethylphosphonium bisulfate [PC₄₄₄₂][HSO₄] | tributylethylphosphonium sulfate [PC₄₄₄₂]₂[SO₄] |
| 7 | trihexylmethylphosphonium bisulfate [PC₆₆₆₁][HSO₄] | trihexylmethylphosphonium sulfate [PC₆₆₆₁]₂[SO₄] |
| 8 | tris(dimethylamino)methylphosphonium bisulfate [C₁hmpt][HSO₄] | tris(dimethylamino)methylphosphonium sulfate [C₁hmpt]₂[SO₄] |
| 9 | tris(dimethylamino)ethylphosphonium bisulfate | tris(dimethylamino)ethylphosphonium sulfate |

| | -continued | |
|---|---|---|
| 10 | ethyltrimethoxyphosphonium bisulfate [C₂hmpt][HSO₄] | ethyltrimethoxyphosphonium sulfate [C₂hmpt]₂[SO₄] |
| 11 | [P(Et)(OMe)₃][HSO₄] | [P(Et)(OMe)₃]₂[SO₄] |
| 12 | ethyltrimethylsulfonium bisulfate [C₂dms][HSO₄] | ethyltrimethylsulfonium sulfate [C₂dms]₂[SO₄] |
| | trimethylsulfoxonium bisulfate [C₁dmso][HSO₄] | trimethylsulfoxonium sulfate [C₁dmso]₂[SO₄] |

ALICYCLIC EXAMPLES

| Ex. No. | | I | | | II | | | III |
|---|---|---|---|---|---|---|---|---|
| | $X^1$ | $X^2$ | name | CAS no | z | n | CAS no | |
| 13 | NMe | none | N-methylpyrrolidine mpy | | Et | Et | | N-ethyl-N-methylpyrrolidinium ethylsulfate [C₂mpy][EtOSO₃] |
| 14 | NMe | none | N-methylpyrrolidine mpy | | Bu | Bu | | N-butyl-N-methylpyrrolidinium butylsulfate [C₄mpy][BuOSO₃] |
| 15 | NEt | none | N-ethylpyrrolidine | | Me | Me | | N-ethyl-N-methylpyrrolidinium methylsulfate [C₂mpy][MeOSO₃] |
| 16 | NBu | none | N-butylpyrrolidine | | Me | Me | | N-butyl-N-methylpyrrolidinium methylsulfate [C₄mpy][MeOSO₃] |
| 17 | NMe | O | N-methylmorpholine mmm | | Et | Et | | N-ethyl-N-methylmorpholinium ethylsulfate [C₂mmm][EtOSO₃] |
| 18 | NMe | O | N-methylmorpholine | | Bu | Bu | | N-butyl-N-methylmorpholinium butylsulfate |

| Ex. No. | | | | |
|---|---|---|---|---|
| 19 | NBu | O | mmm | N-butylmorpholine 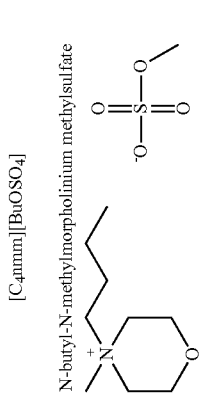 [C₄mmm][BuOSO₄] N-butyl-N-methylmorpholinium methylsulfate 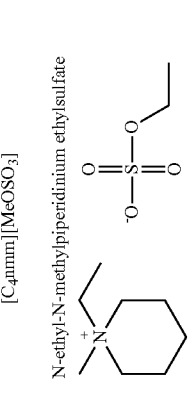 [C₄mmm][MeOSO₃] |
| 20 | NMe | CH₂ | mpp Et Et | N-methylpiperidine N-ethyl-N-methylpiperidinium ethylsulfate 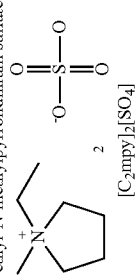 [C₂mpp][EtOSO₃] |

| Ex. No. | IV | V |
|---|---|---|
| 13 | N-ethyl-N-methylpyrrolidinium bisulfate 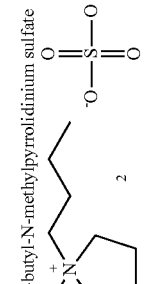 [C₂mpy][HSO₄] | N-ethyl-N-methylpyrrolidinium sulfate [C₂mpy]₂[SO₄] |
| 14 | N-butyl-N-methylpyrrolidinium bisulfate  [C₄mpy][HSO₄] | N-butyl-N-methylpyrrolidinium sulfate [C₄mpy]₂[SO₄] |
| 15 | N-ethyl-N-methylpyrrolidinium bisulfate | N-ethyl-N-methylpyrrolidinium sulfate |

| | | |
|---|---|---|
| 16 | [C₂mpy][HSO₄]<br>N-ethyl-N-methylpyrrolidinium bisulfate | [C₂mpy]₂[SO₄]<br>N-ethyl-N-methylpyrrolidinium sulfate |
| 17 | [C₄mpy][HSO₄]<br>N-butyl-N-methylpyrrolidinium bisulfate | [C₄mpy]₂[SO₄]<br>N-butyl-N-methylpyrrolidinium sulfate |
| 18 | [C₂mmm][HSO₄]<br>N-ethyl-N-methylmorpholinium bisulfate | [C₂mmm]₂[SO₄]<br>N-ethyl-N-methylmorpholinium sulfate |
| 19 | [C₄mmm][HSO₄]<br>N-butyl-N-methylmorpholinium bisulfate | [C₄mmm]₂[SO₄]<br>N-butyl-N-methylmorpholinium sulfate |
| 20 | [C₄mmm][HSO₄]<br>N-ethyl-N-methylpiperidinium bisulfate | [C₄mmm]₂[SO₄]<br>N-ethyl-N-methylpiperidinium sulfate |

-continued

| | |
|---|---|
| [C₂mpp][HSO₄] | [C₂mpp]₂[SO₄] |

ALICYCLIC EXAMPLES

| Ex. No. | X¹ | X² | I name | CAS no | II z | n | CAS no | III |
|---|---|---|---|---|---|---|---|---|
| 21 | NMe | NMe | N,N'-dimethylpiperazine dmpz | | Et | Et | | N-ethyl-N,N'-dimethylpiperazinium ethylsulfate [C₂dmpz][EtOSO₃] |
| 22 | NMe | S | N-methylthiomorpholine mmtm | | Et | Et | | N-ethyl-N-methylthiomorpholinium ethylsulfate [C₂mmtm][EtOSO₃] |
| 23 | NMe | SO₂ | N-methiomorpholine-4,4-dioxide mmtmO₂ | | Et | Et | | N-ethyl-N-methylthiomorpholinium-4,4-dioxide ethylsulfate [C₂mmtmO₂][EtOSO₃] |
| 24 | S | O | 1,4-thioxane | | Et | Et | | S-ethyl-1,4-thioxanium ethylsulfate |

-continued

| Ex. No. | | | |
|---|---|---|---|
| 25 | SO | O | thx <br> 1,4-thioxane-1-oxide thxO | 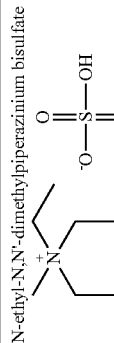 S-ethyl-1,4-thioxanium-1-oxide ethylsulfate [C₃thxO][EtOSO₃] |

| Ex. No. | IV | V |
|---|---|---|
| 21 | 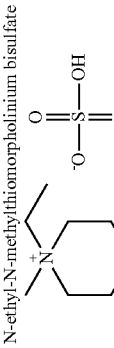 N-ethyl-N,N'-dimethylpiperazinium bisulfate [C₂dmpz][HSO₄] | 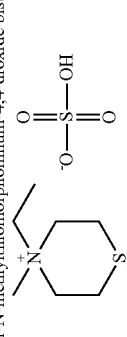 N-ethyl-N,N'-dimethylpiperazinium sulfate [C₂dmpz]₂[SO₄] |
| 22 | 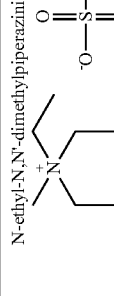 N-ethyl-N-methylthiomorpholinium bisulfate [C₂nmtm][HSO₄] | 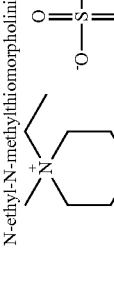 N-ethyl-N-methylthiomorpholinium sulfate [C₂nmtm]₂[SO₄] |
| 23 | 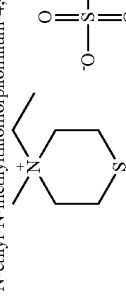 N-ethyl-N-methylthiomorpholinium-4,4-dioxide bisulfate [C₂nmtmO₂][HSO₄] | 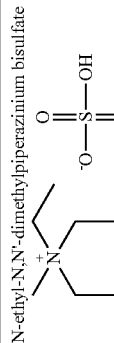 N-ethyl-N-methylthiomorpholinium-4,4-dioxide sulfate [C₂nmtmO₂]₂[SO₄] |

| | | |
|---|---|---|
| 24 | S-ethyl-1,4-thioxanium bisulfate<br>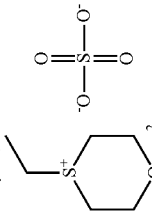<br>[C₂thx][HSO₄] | S-ethyl-1,4-thioxanium sulfate<br><br>[C₂thx]₂[SO₄] |
| 25 | S-ethyl-1,4-thioxanium-1-oxide bisulfate<br>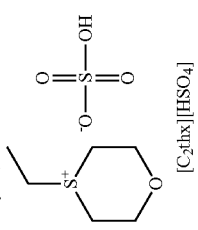<br>[C₂thxO][HSO₄] | S-ethyl-1,4-thioxanium-1-oxide sulfate<br>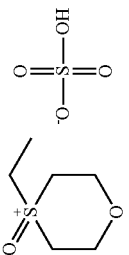<br>[C₂thxO]₂[SO₄] |

AROMATIC EXAMPLES

| Ex. No. | I X | R¹ | R² | R³ | name | II CAS no | z | n | CAS no | III | |
|---|---|---|---|---|---|---|---|---|---|---|---|
| 26 | NMe | none | none | none | 1-methylimidazole mim | | Et | Et | | 1-ethyl-3-methylimidazolium ethylsulfate [C₂mim][EtOSO₃] | |
| 27 | NBu | none | none | none | 1-butylimidazole | | Me | Me | | 1-butyl-3-methylimidazolium methylsulfate [C₄mim][MeOSO₃] | |
| 28 | NMe | Me | none | none | 1,2-dimethylimidazole dmim | | Et | Et | | 1-ethyl-2,3-dimethylimidazolium ethylsulfate [C₂dmim][EtOSO₃] | |
| 29 | NMe | NMe₂ | none | none | 2-dimethylaminomethylimidazole dmami | | Me | Me | | 1,3-dimethyl-2-dimethylaminoimidazolium methylsulfate [C₁dmami][MeOSO₃] | |
| 30 | NEt | none | Me | CH₂OH | 1-ethyl-4(5)-methyl-5(4)- | | Et | Et | | 1,3-diethyl-5-methyl-4-imidazoliumethanol methylsulfate | |

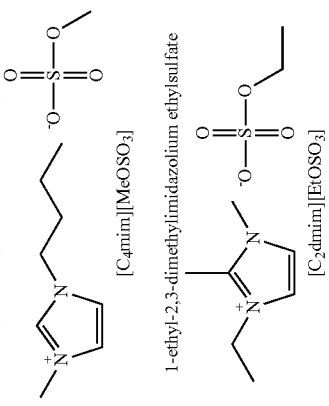

| Ex. No. | IV | V |
|---|---|---|
| 26 | 1-ethyl-3-methylimidazolium bisulfate [C₂mim][HSO₄] | 1-ethyl-3-methylimidazolium sulfate [C₂mim]₂[SO₄] |
| 27 | 1-butyl-3-methylimidazolium bisulfate [C₄mim][HSO₄] | 1-butyl-3-methylimidazolium sulfate [C₄mim]₂[SO₄] |
| 28 | 1-ethyl-2,3-dimethylimidazolium bisulfate [C₂dmim][HSO₄] | 1-ethyl-2,3-dimethylimidazolium sulfate [C₂dmim]₂[SO₄] |
| 29 | 1,3-dimethyl-2-dimethylaminoimidazolium bisulfate | 1,3-dimethyl-2-dimethylaminoimidazolium sulfate |
| 31 | imidazolemethanol | N-ethylpyridinium ethylsulfate [C₂py][EtOSO₃] |
|    | pyridine py | |

| | -continued | |
|---|---|---|
| 30 | 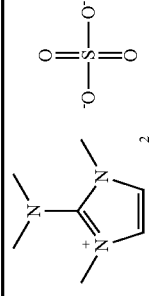
1,3-diethyl-5-methyl-4-imidazoliummethanol bisulfate
[----][----] | 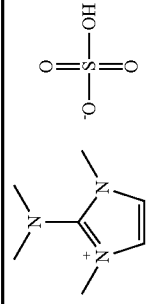
1,3-diethyl-5-methyl-4-imidazoliummethanol sulfate
[----][----] |
| 31 | 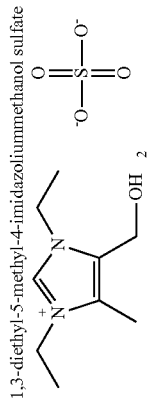
N-ethylpyridinium bisulfate
[C₂py][HSO₄] | 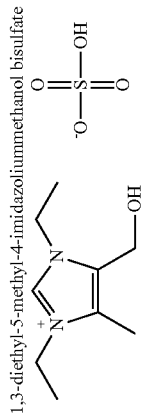
N-ethylpyridinium sulfate
[C₂py]₂[SO₄] |

AROMATIC EXAMPLES

| Ex. No. | I | | | | | II | | | III |
|---|---|---|---|---|---|---|---|---|---|
| | X | R¹ | R² | R³ | name | CAS no | z | n | CAS no |
| 32 | S | none | none | Me | 4-methylthiazole 4mtz | | Et | Et | 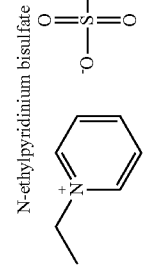
3-ethyl-4-methylthiazolium ethylsulfate
[C₂4mtz][EtOSO₃] |
| 33 | S | none | CH₂CH₂OH | Me | 4-methyl-5-thiazoleethanole | | Et | Et | 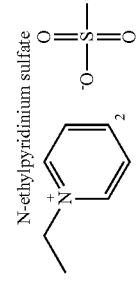
3-ethyl-4-methyl-5-thiazoliumethanol ethylsulfate |

-continued

| | | | | IV | |
|---|---|---|---|---|---|
| 34 | CH | none | none | imidazo[1,2-a]pyridine impd | Me Me | 3-methylimidazo[1,2-a]pyridinium methylsulfate [C₁impd][MeOSO₃] |
| 35 | N | none | none | imidazo[1,2-a]pyrimidine impm | Me Me | 3-methylimidazo[1,2-a]pyrimidinium methylsulfate [C₁impm][MeOSO₃] |

| Ex. No. | IV | V |
|---|---|---|
| 32 | 3-ethyl-4-methylthiazolium bisulfate [C₂4mtz][HSO₄] | 3-ethyl-4-methylthiazolium sulfate [C₂4mtz]₂[SO₄] |
| 33 | 3-ethyl-4-methyl-5-thiazoliumethanol bisulfate | 3-ethyl-4-methyl-5-thiazoliumethanol sulfate |
| 34 | 3-methylimidazo[1,2-a]pyridinium methylsulfate | 3-methylimidazo[1,2-a]pyridinium methylsulfate |

-continued
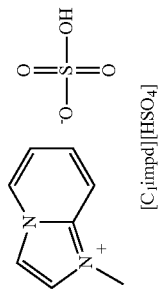
[C₁impd][HSO₄]
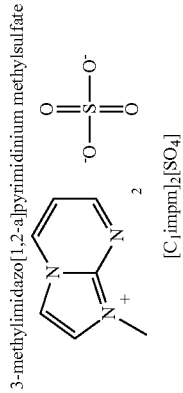
[C₁impd]₂[SO₄]
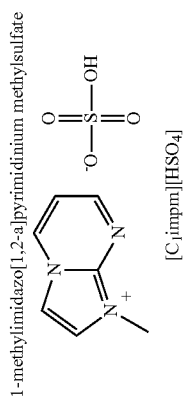
1-methylimidazo[1,2-a]pyrimidinium methylsulfate
[C₁impm][HSO₄]
3-methylimidazo[1,2-a]pyrimidinium methylsulfate
[C₁impm]₂[SO₄]

As seen from the tables above, a variety of sulfate salts can be prepared in accordance with the methods described herein. These sulfate salts can in turn be converted into ionic liquids by reacting the sulfate salt with a salt of a desired anion to produce ionic liquids with the cation of the heteroatomic compound and the desired anion.

Example 36

[$C_1$impd][ise] is an ionic liquid comprised of 1-methylimidazo[1,2-a]pyridinium ($C_1$impd) as the cation and isethionate (ise) as the anion. The ionic liquid cation was prepared by preparing the cation in accordance with Example 34. Specifically, [$C_1$impd]$_2$[SO$_4$] (3.166 g, 8.74 mmol) was prepared from imidazo[1,2-a]pyridine and dimethylsulfate in accordance with Example 34 in the table above, and as shown below:

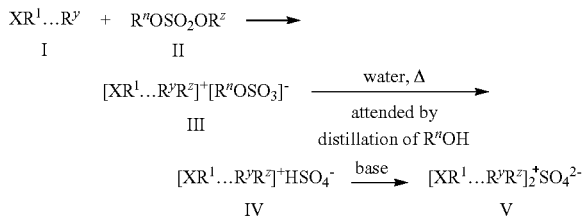

where $XR^1 \ldots R^y$ is imidazo[1,2-$\alpha$]pyridine (impd), and $R''OSO_2OR^z$ is dimethyl sulfate. Reaction Product III is:

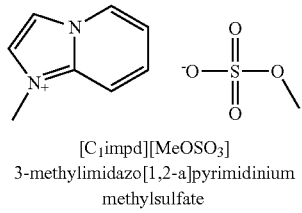

[$C_1$impd][MeOSO$_3$]
3-methylimidazo[1,2-a]pyrimidinium methylsulfate

Reaction product IV is:

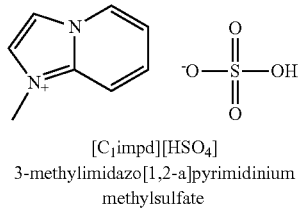

[$C_1$impd][HSO$_4$]
3-methylimidazo[1,2-a]pyrimidinium methylsulfate

Reaction product V is:

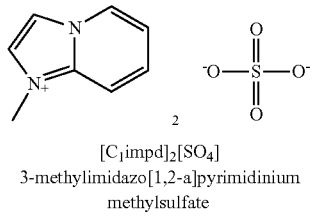

[$C_1$impd]$_2$[SO$_4$]
3-methylimidazo[1,2-a]pyrimidinium methylsulfate

Reaction product V, [$C_1$impd]$_2$[SO$_4$] (3.166 g, 8.74 mmol) was dissolved in 2:1 alcohol-water (30 mL), whereupon a prepared solution of sodium isethionate (2.592 g, 17.50 mmol) in 2:1 alcohol-water (18 mL) was added to it with stirring. The resulting slurry was stirred for about 2 h, whereupon it was suction filtered, and the filtrate was concentrated as far as feasible by rotary evaporation. The residue was taken up in methanol (25 mL) and loaded onto an about 12-g column of 230-400 mesh silica gel previously packed in methanol.

The methanolic solution of crude [$C_1$impd][ise] was pushed down to the level of, the top of the silica gel bed with air pressure while the column issue was collected in a 250-mL round bottom flask; the flask previously containing the crude product was rinsed with methanol (25 mL) and the rinse methanol was similarly loaded and pressed down while the column issue was collected on top of the first fraction. The rinsing process was repeated once before the silica gel column was washed down with fresh methanol (125 mL), all the while collecting the column issue on top of the accumulated methanol solution. The combined methanolic fractions were concentrated by rotary evaporation to produce purified [$C_1$impd][ise] (4.122 g, 15.96 mmol, 91%) as an ionic liquid. The ionic liquid of Example 11 slowly solidified at ambient conditions. Specifically, it was freely liquid when contained in a flask immersed in an 80° C. water bath; it remained liquid for several hours after it was removed from the water bath. Thereafter, several regions of the liquid began to slowly solidify independently of each other, and after about 1 day, the IL had turned thoroughly solid under ambient conditions.

The embodiments and examples have been provided solely to illustrate embodiments of the invention and should not be considered limiting. To the contrary, the embodiments encompass all modifications, substitutions, alterations, and equivalents with in the spirit and scope described herein.

The invention claimed is:

1. A method for preparing an ionic liquid that includes a heteroatomic compound comprising:
   (1) reacting a heteroatomic compound with an excess of dialkyl sulfate to produce an alkylsulfate salt of the heteroatomic compound;
   (2) hydrolyzing the alkylsulfate salt to produce a bisulfate salt of the heteroatomic compound;
   (3) neutralizing the bisulfate salt to produce the sulfate salt of the heteroatomic compound; and
   (4) reacting the sulfate salt of the heteroatomic compound with a salt of a desired anion to produce an ionic liquid comprising the cation of the heteroatomic compound and the desired anion.

2. The method of claim 1, wherein the heteroatomic compound is selected from the group consisting of pyrrolidines, morpholines, piperidines, piperazines, quinuclidines, bicyclic amines, amidines, guanidines, alkanolamines, monoalkylamines, dialkylamines, trialkylamines, pyrroles, imidazoles, pyrazoles, triazoles, thiazoles, oxazoles, pyridines, imidazopyridines, imidazopyrimidines, monoalkylphosphines, dialkylphosphines, trialkylphosphines, monoalkylphosphites, dialkylphosphites, trialkylphosphites, phosphorus monoamines, phosphorus diamines, phosphorus triamines, mercaptans, thiophenes, dihydrothiophenes, tetrahydrothiophenes, thioethers, dialkylsulfoxides, and combinations thereof.

3. The method of claim 1, wherein the dialkyl sulfate is represented by the formula $R''OSO_2OR^z$, wherein $R''$ and $R^z$ may be the same or different and represent an alkyl group.

4. The method of claim 3, wherein the symmetric dialkyl sulfate is selected from the group consisting of dimethyl sulfate and diethyl sulfate.

5. The method of claim 1, wherein hydrolyzing comprises reacting the alkylsulfate salt with water.

6. The method of claim 5, wherein hydrolyzing comprises applying heat to the reaction.

7. The method of claim 5, wherein hydrolyzing comprises producing an alcohol byproduct.

8. The method of claim 7, wherein the hydrolyzing comprises removing the alcohol byproduct by distillation.

9. The method of claim 1, wherein the neutralizing comprises reacting a base with the bisulfate salt.

10. The method of claim 9, wherein the base is sodium bicarbonate.

11. The method of claim 1, wherein the salt of a desired anion is a sodium salt.

12. The method of claim 1, wherein reacting the sulfate salt of the heteroatomic compound with a salt of a desired anion is performed in a mixture of an organic solvent and water.

13. The method of claim 12, wherein the organic solvent is an organic solvent that is at least 5 wt % soluble in water.

14. The method of claim 12, wherein the organic solvent is selected from the group consisting of alcohols, reagent alcohol, diethers, cyclic ethers, and mixtures thereof.

15. The method of claim 12, wherein the mixture of organic solvent and water is in a ratio of approximately 2 parts organic solvent to 1 part water.

16. The method of claim 1, wherein (1)-(3) comprises:
(1) reacting N-methylmorpholine with an excess of diethylsulfate to produce the ethyl sulfate salt with the following structure:

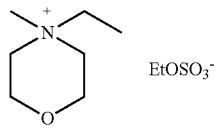

(2) hydrolyzing the ethyl sulfate salt of N-methylmorpholine to produce the bisulfate salt with the following structure:

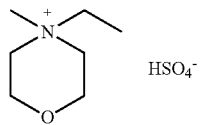

and
(3) neutralizing the bisulfate salt to produce N-ethyl-N-methylmorpholinium sulfate.

17. The method of claim 1, wherein (1)-(3) comprises:
(1) reacting N-ethylmorpholine with an excess of dimethylsulfate to produce the methyl sulfate salt with the following structure:

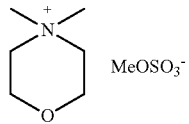

(2) hydrolyzing the methyl sulfate salt of N-ethylmorpholine to produce the salt with the following structure:

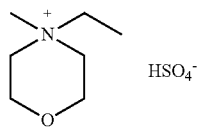

and
(3) neutralizing the bisulfate salt to produce N-ethyl-N-methylmorpholinium sulfate.

18. The method of claim 1, wherein (1)-(3) comprises:
(1) reacting 1,2-dimethylimidazole with an excess of diethylsulfate to produce the ethyl sulfate salt with the following structure:

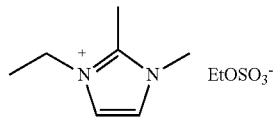

(2) hydrolyzing the ethyl sulfate salt of 1-ethyl-2-methylimidazole to produce the bisulfate salt with the following structure:

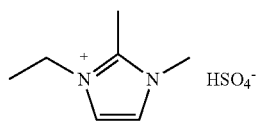

and
(3) neutralizing the bisulfate salt to produce 1-ethyl-2,3-dimethylimidazolium sulfate.

19. The method of claim 1, wherein (1)-(3) comprises:
(1) reacting 3-dimethylamino-2,2-dimethyl-1-propanol with an excess of dimethylsulfate to produce the methyl sulfate salt with the following structure:

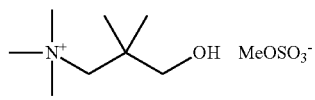

(2) hydrolyzing the methyl sulfate salt of 1-ethyl-2-methylimidazole to produce the bisulfate salt with the following structure:

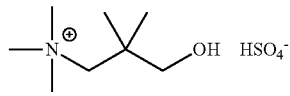

and
(3) neutralizing the bisulfate salt to produce 1-propanaminium, 2-(hydroxymethyl)-N,N,N,2-tetramethyl-sulfate having the following structure:

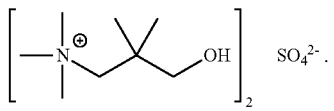

* * * * *